United States Patent [19]

Wysong

[11] Patent Number: 5,760,192
[45] Date of Patent: Jun. 2, 1998

[54] MULTI-COMPONENT LIQUID AZODINITRILE MIXTURES

[75] Inventor: Ernest Byron Wysong, Hockessin, Del.

[73] Assignee: E. I. du Pont de Nemours and Company, Wilmington, Del.

[21] Appl. No.: 672,817

[22] Filed: Jun. 28, 1996

Related U.S. Application Data

[60] Provisional application No. 60/003,270, Aug. 29, 1995.

[51] Int. Cl.[6] .................................................. C07C 245/04
[52] U.S. Cl. ........................... 534/578; 534/838; 502/167
[58] Field of Search ........................ 534/838; 502/167; 252/186.44

[56] References Cited

U.S. PATENT DOCUMENTS

| | | |
|---|---|---|
| 3,987,025 | 10/1976 | Moore, Jr. ................................. 534/838 |
| 4,028,345 | 6/1977 | Moore, Jr. ................................. 534/878 |
| 4,039,527 | 8/1977 | Nagaoka et al. .......................... 534/838 |
| 4,061,590 | 12/1977 | Moore, Jr. ................................. 502/167 |

*Primary Examiner*—Fiona T. Powers

[57] ABSTRACT

An azodinitrile composition comprising a mixture of at least six different azodinitriles of formula I

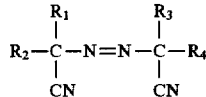

wherein $R_1$, $R_2$, $R_3$, and $R_4$ are each independently acyclic aliphatic hydrocarbon radicals of 1–9 carbon atoms, said mixture having a freezing point of a maximum of 25° C. and a process for its preparation are disclosed.

8 Claims, 4 Drawing Sheets

MULTI-COMPONENT LIQUID AZODINITRILE MIXTURES

RELATED APPLICATIONS

This application claims the benefit of U.S. Provisional Application No. 60/003,270, filed Aug. 29, 1995 by the same inventor.

FIELD OF THE INVENTION

The present invention relates to multicomponent azodinitrile mixtures which are liquid below 25° C. for use as free radical polymerization initiators in various polymerization reactions.

BACKGROUND OF THE INVENTION

Azodinitrile compounds represent an important class of free-radical initiating agents which are used in a variety of industrial applications. Examples of such applications include: vinyl polymerizations, graft polymerizations, halogenations, and blowing agents. With respect to peroxide based initiators, azodinitriles display consistent decomposition behavior, less color formation, and a higher degree of safety.

Azodinitrile compounds can be either symmetrical or asymmetrical about the azo linkage. Symmetrical azo initiators of commercial interest are generally solid and have low to medium solubility in organic solvents. Asymmetrical azo initiators, by contrast, are often low melting solids with higher solubilities in organic solvents. Polymer manufacturers have long sought liquid azodinitrile initiators to eliminate the problems associated with the commercially available, solid azodinitriles such as dusting, ergonomics, and inability to add via screw feeders. A liquid azodinitrile compound or mixture of compounds with a melting point of 0° C. or lower, preferably −15° C., would be ideal for many commercial applications. In addition, a liquid azo mixture which facilitates polymerizations using little or no solvent for low volatile organic compound coatings is desirable.

U.S. Pat. No. 3,987,025 of Moore issued Oct. 19, 1976 discloses liquid mixtures of symmetric and asymmetric azodinitrile compounds with a maximum freezing point of 25° C. The starting aminonitriles are limited to two and to those having unbranched hydrocarbon groups. This patent also suggests that it is possible to prepare liquid azodinitrile mixtures when more than two aminonitrile starting materials are used, and that liquid azodinitrile mixtures will be highly favored as the number of aminonitriles is increased above two. However, not all mixtures prepared using more than two aminonitriles are liquids at 25° C., and Moore does not teach any such mixtures.

Many synthetic routes are known for preparation of azodinitriles via reaction of a ketone with a hydrazine compound to generate a hydrazo compound which is then oxidized to azodinitrile. A second approach reacts a cyanohydrin of a ketone with ammonia to form an aminonitrile and oxidatively coupling the aminonitrile to form an azodinitrile. Aliphatic azodinitriles can be prepared by reacting a metal hypochlorite with an aminonitrile in water containing a surfactant. These syntheses do not specifically address how to obtain mixtures prepared from more than two aminonitriles which are liquid at low temperatures. Such mixtures are desirable for use as free-radical initiating agents in industrial applications.

SUMMARY OF THE INVENTION

The present invention comprises an azodinitrile composition and a process for the preparation comprising a mixture of at least six different azodinitriles of formula I

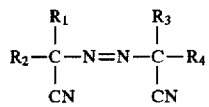

wherein $R_1$, $R_2$, $R_3$, and $R_4$ are each independently selected from the group consisting of acyclic aliphatic hydrocarbon radicals of 1–9 carbon atoms, preferably 4–9 carbon atoms, said mixture having a freezing point of a maximum of 25° C. Preferably the compositions are liquid at and have a maximum freezing point of 0° C. to −15° C.

The present invention further comprises a process for the preparation of azodinitrile mixtures comprising reacting three or more different aminonitriles of formula

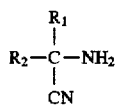

wherein $R_1$ and $R_2$ are each independently selected from the group consisting of acyclic aliphatic hydrocarbon radicals of 1–9 carbon atoms, with 5% to 15% by weight based on the reaction mixture of a metal hypochlorite, M(OCl)x, wherein M is selected from the group consisting of sodium, potassium, or calcium, and x is the valence of M, in an aqueous medium in the presence of 0.25 to 10% by weight based on the weight of aminonitrile of a surface active compound or mixtures thereof having a hydrophilic-lipophilic balance of 8 to 35 at a temperature of −10° C. to 30° C., said metal hypochlorite and alpha-aminonitrile being present in an equivalent ratio of from 1:1 to 2:1 of hypochlorite to aminonitrile and recovering from the reaction product a mixture of aliphatic azodinitrile compounds of the formula

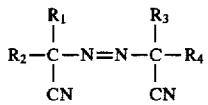

wherein $R_1$, $R_2$, $R_3$, and $R_4$ are each independently selected from the group consisting of acyclic aliphatic hydrocarbon radicals of 1–9 carbon atoms.

BRIEF DESCRIPTION OF THE DRAWING

FIG. 1 depicts a phase diagram showing the concentration ranges of aminonitrile reactants as detailed in Example 1 which yield liquid mixtures at −15° C. for a mixture of.

Figure 1:
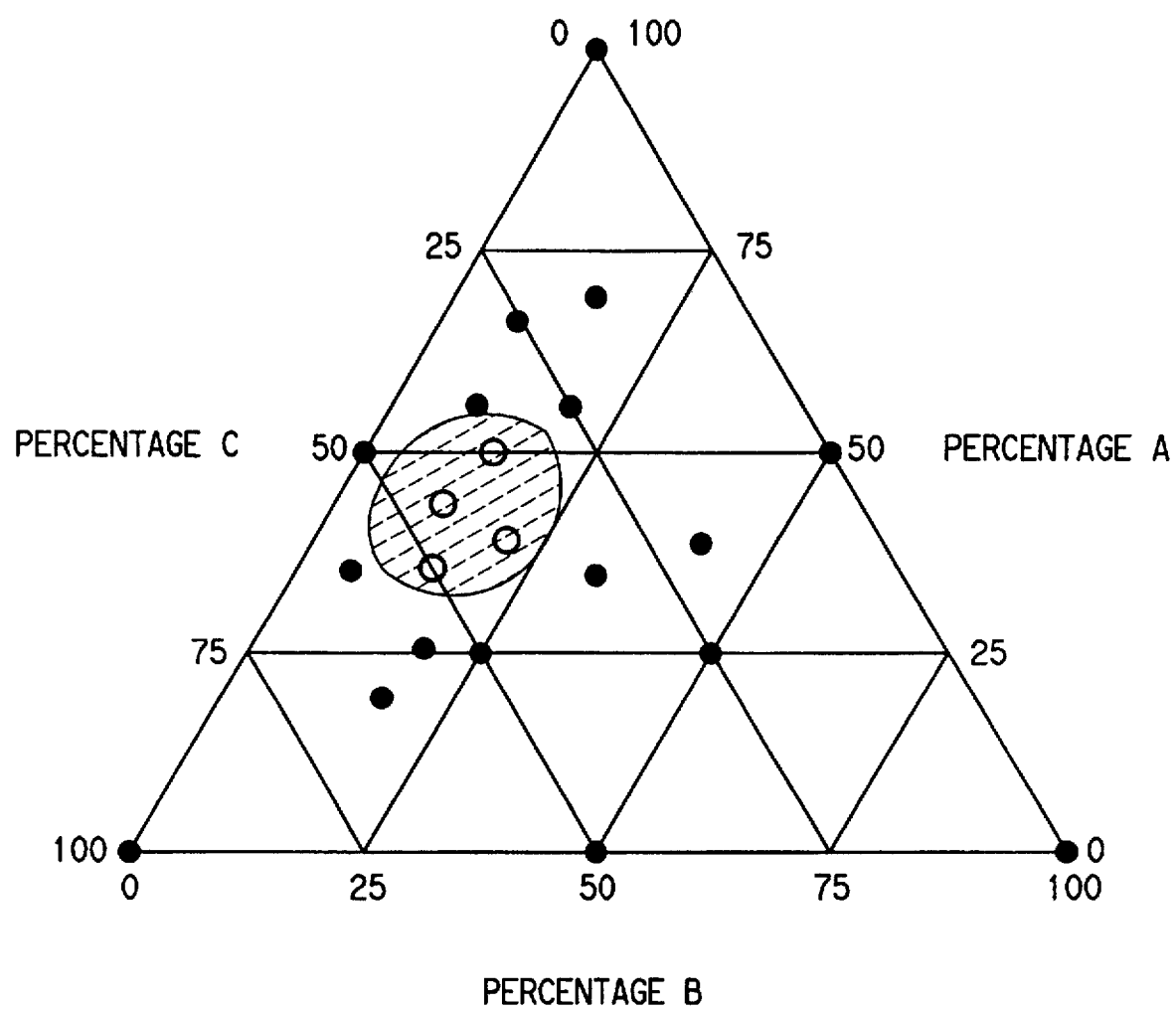
Figure 2:
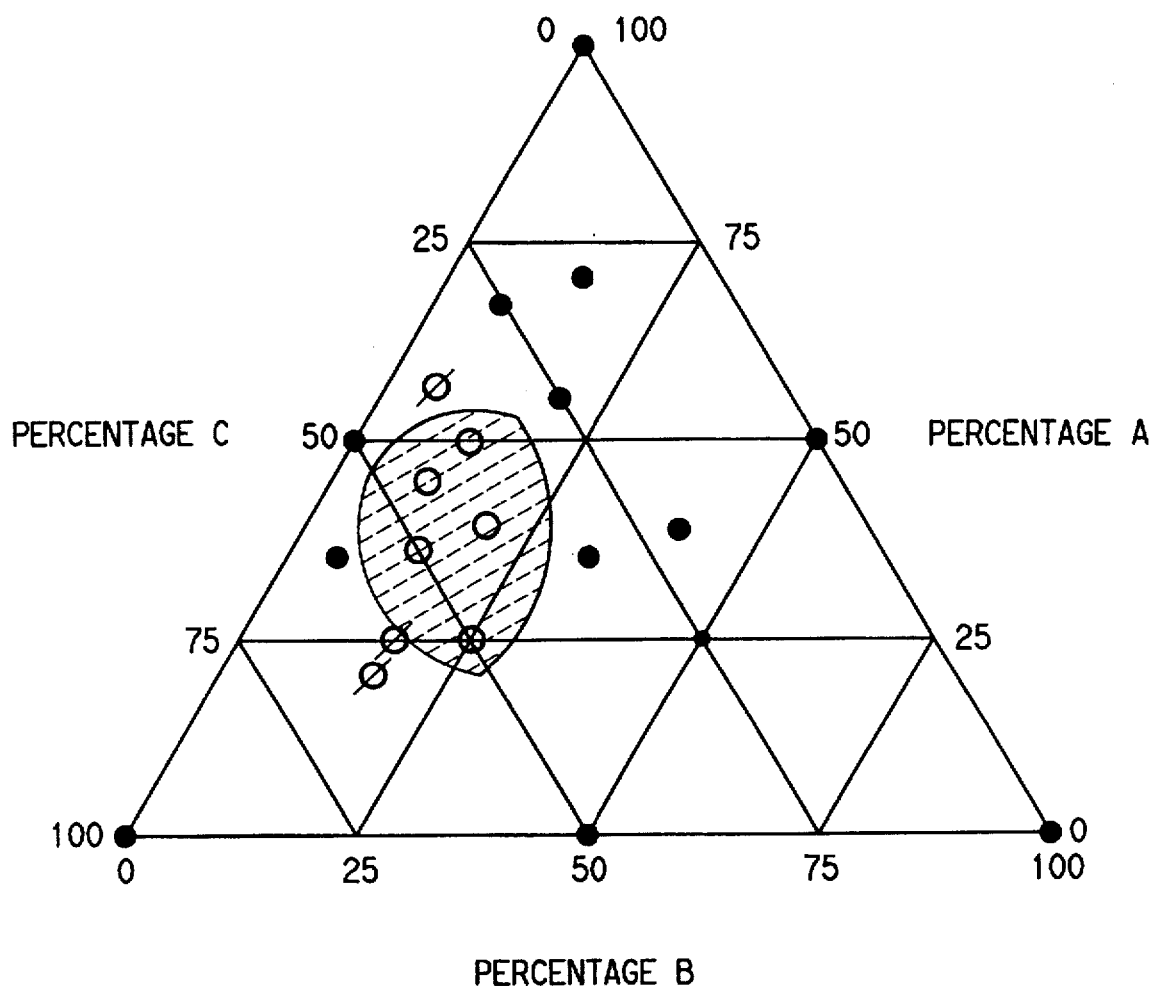

Butanenitrile, 2,2'-azobis(2-methyl-Pentanenitrile, 2,2'-azobis(2-methyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Pentanenitrile, 2-[(1-cyano-1-methylpropyl)azo]-2-methyl FIG. 2 depicts a phase diagram showing the concentration of aminonitrile reactants which yield liquid mixtures of azodinitriles at 20° C. for the same product mixture as defined for FIG. 1.

Figure 3:
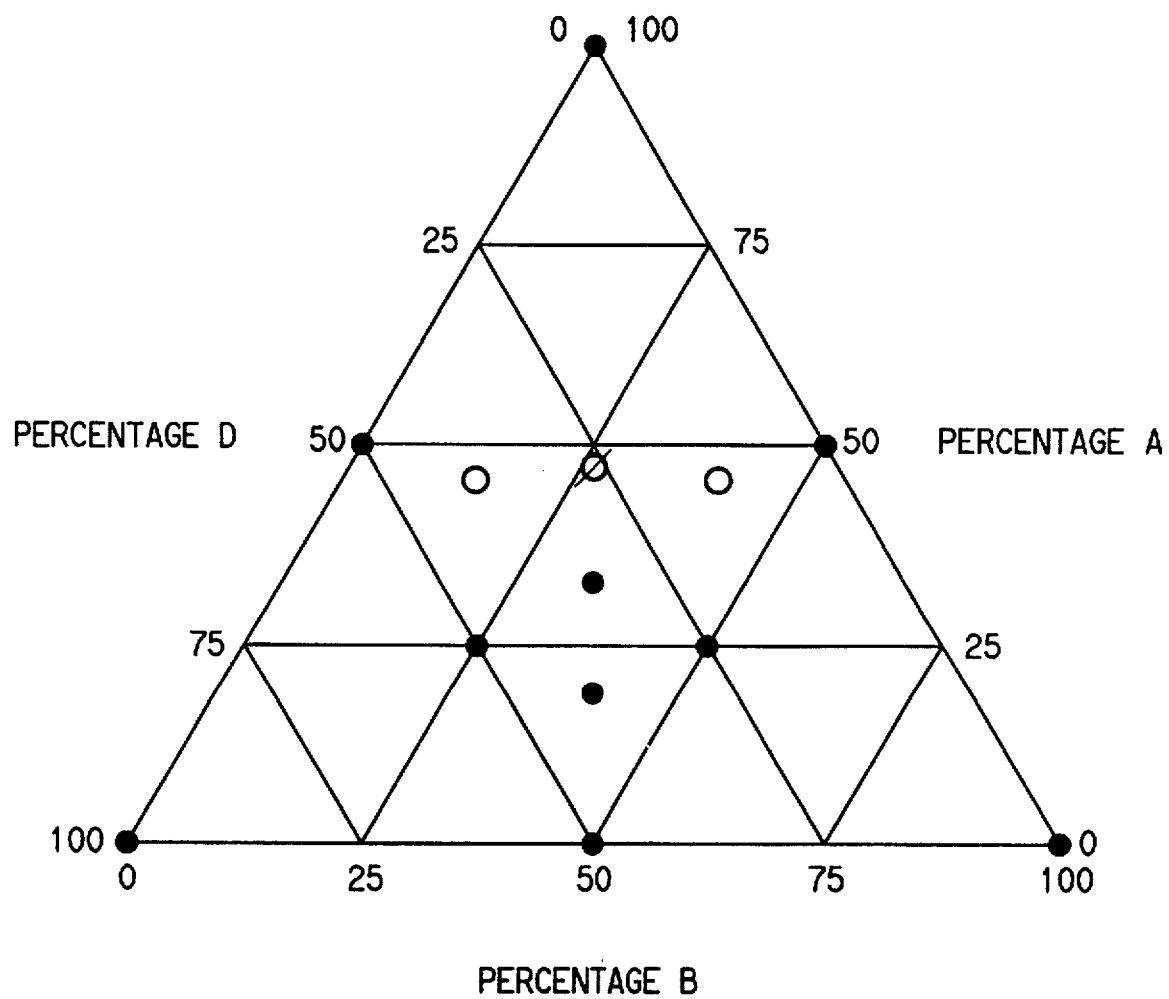
Figure 4:
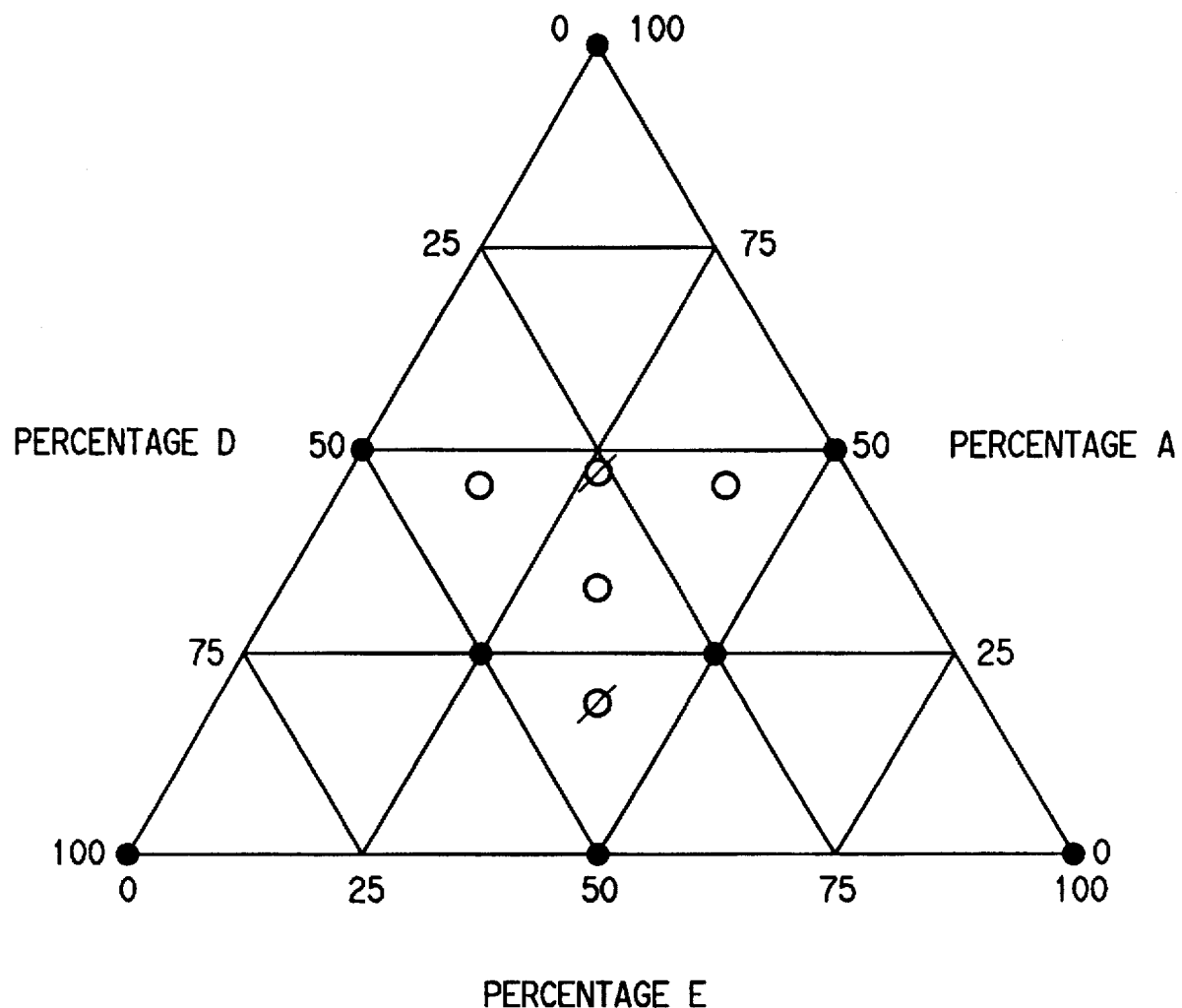

FIG. 3 depicts a phase diagram showing the concentration ranges of aminonitrile reactants as detailed in Example 2 which yield liquid mixtures at –15° C. for a mixture of Butanenitrile, 2,2'-azobis(2-methyl-Pentanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylbutyl)azo]-2-methyl-Pentanenitrile, 2-[(1-cyano-1-methylpropyl)azo]-2-methyl FIG. 4 depicts a phase diagram showing the concentration ranges of aminonitrile reactants as detailed in Example 3 which yield liquid mixtures at 7° C. for a mixture of Butanenitrile, 2,2'-azobis(2-methyl-Heptanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylhexyl)azo]-2-methyl-Heptanenitrile, 2-[(1-cyano-1-methylpropyl)azo]-2-methyl

DETAILED DESCRIPTION OF THE INVENTION

The present invention comprises a mixture of azodinitrile compounds such that liquid behavior is obtained at temperatures at or below 25° C. Preferably the mixtures have a maximum freezing point of 0° C., and more preferably –15° C. The compositions contain both symmetrical and asymmetrical azodinitrile compounds.

The compositions of the present invention are prepared from three or more aminonitriles. The particular azodinitrile product mixture obtained depends upon the aminonitrile starting materials employed.

Starting with three different aminonitriles

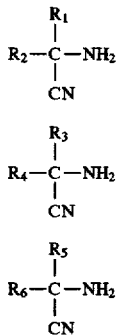

wherein $R_1$, $R_2$, $R_3$, $R_4$, $R_5$, and $R_6$ are each independently selected from the group consisting of acyclic aliphatic hydrocarbon radicals of 1–9 carbon atoms results in an azodinitrile mixture comprising symmetric products such as

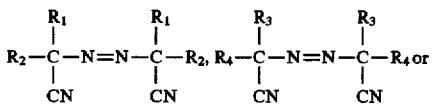

-continued

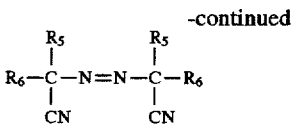

and asymmetric products such as

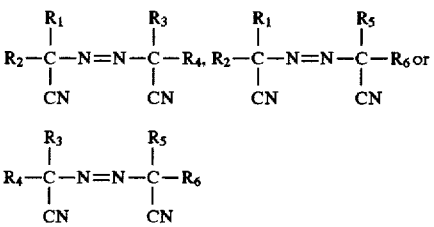

It can easily be determined that when starting with three different aminonitriles that there will be three different symmetric azodinitriles, and three different asymmetrical azodinitriles. When starting with four different aminonitriles there will be four different symmetric azodinitriles, and six different asymmetrical azodinitriles. In the general case when starting with n different aminonitriles there will be n different symmetric azodinitriles, and n!/2(n–2)! different asymmetrical azodinitriles in the resulting product.

Suitable acyclic aliphatic hydrocarbon radicals for $R_1$, $R_2$, $R_3$, $R_4$, $R_5$ and $R_6$ include, for example, methylbutyro, methylpentano, methylheptano, methyloctano, ethylbutano, cyanomethylpropyl, cyanomethylbutyl, and cyanodimethylbutyl.

Preferred azodinitrile compositions of the present invention are liquid at and have a maximum freezing point of 25° C. and include mixture A as follows:

A. Butanenitrile, 2,2'-azobis(2-methyl-Pentanenitrile, 2,2'-azobis(2-methyl-Butanenitrile, 2,2'-azobis(2-ethyl-Pentanenitrile, 2-[(1-cyano-1-methylpropyl)azo]-2-methyl-Pentanenitrile, 2-[(1-cyano-1-ethylpropyl)azo]-2-methyl-Butanenitrile, 2-[(1-cyano-1-methylpropyl)azo]-2-ethyl Also preferred is the following mixture B of the present invention having a maximum freezing point of 7° C.

B. Butanenitrile, 2,2'-azobis(2-methyl-Heptanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylhexyl)azo]-2-methyl-Heptanenitrile, 2-[(1-cyano-1-methylpropyl)azo]-2-methyl More preferred azodinitrile compositions of the present invention are liquid at and have a maximum freezing point of 0° C. and include mixtures C and D as follows:

C. Pentanenitrile, 2,2'-azobis(2-methyl-Butanenitrile, 2,2'-azobis(2-ethyl-Heptanenitrile, 2,2'-azobis(2-methyl-Heptanenitrile, 2-[(1-cyano-1-methylbutyl)azo]-2-methyl-Heptanenitrile, 2-[(1-cyano-1-ethylpropyl)azo]-2-methyl-Pentanenitrile, 2-[(1-cyano-1-ethylpropyl)azo]-2-methyl D. Butanenitrile, 2,2'-azobis(2-methyl-Pentanenitrile, 2,2'-azobis(2-methyl-Pentanenitrile, 2,2'-azobis(2,4-dimethyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Heptanenitrile, 2-[(1-cyano-1,3-dimethylbutyl)azo]-2-methyl-Pentanenitrile, 2-[(1-cyano-1-methylbutyl)azo]-2,4-dimethyl-Pentanenitrile, 2-[(1-cyano-1-methylpropyl)azo]-2- methyl-Pentanenitrile, 2-[(1-cyano-1-methylpropyl) azo]-2,4-dimethyl

More particularly preferred are azodinitrile compositions which are liquid at and have a maximum freezing point of −15° C. and include the following mixtures E, F and G:

E. Butanenitrile, 2,2'-azobis(2-methyl-Pentanenitrile, 2,2'-azobis(2-methyl-Heptanenitrile, 2,2'-azobis(2-methyl-Heptanenitrile, 2-[(1-cyano-1-methylpropyl) azo]-2-methyl-Heptanenitrile, 2-[(1-cyano-1-methylbutyl)azo]-2-methyl-Pentanenitrile, 2-[(1-cyano-1-methylpropyl)azo]-2-methyl F. Butanenitrile, 2,2'-azobis(2-methyl-Pentanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylbutyl)azo]-2-methyl-Pentanenitrile, 2-[(1-cyano-1-methylpropyl) azo]-2-methyl G. Butanenitrile, 2,2'-azobis(2-methyl-Pentanenitrile, 2,2'-azobis(2-methyl-Butanenitrile, 2,2'-azobis(2-ethyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl) azo]-2-methyl-Heptanenitrile, 2-[(1-cyano-1-ethylpropyl)azo]-2-methyl-Pentanenitrile, 2-[(1-cyano-1-methylpropyl)azo]-2-methyl-Pentanenitrile, 2-[(1-cyano-1-ethylpropyl)azo]-2-methyl-Butanenitrile, 2-[(1-cyano-1-methylpropyl)azo]-2-ethyl The ratio of starting aminonitriles can affect the physical phase of the resulting product mixture. FIG. 1 depicts a phase diagram at −15° C. for the above particularly preferred composition E. As detailed in Example 1, this composition is prepared from 2-amino-2methylbutyronitrile (Component A), 2-amino-2methylpentanonitrile (Component B) and 2-amino-2methylheptanonitrile (Component C). The phase diagram of FIG. 1 shows the percentages of each starting aminonitrile, which when reacted, results in a product composition which is liquid at −15° C. The liquid compositions roughly correspond to the lined area. This corresponds to 30–50% by weight of component A, 5–25% by weight of component B, and 30–55% by weight of component C.

FIG. 2 depicts a phase diagram at 20° C. for these same components A, B, and C. The liquid compositions roughly correspond to the lined area which correlates with 20–55% by weight of component A, 5–30% by weight of component B, and 30–55% by weight of component C. Also shown are three data points (∅) which display partial liquid behavior. For these compositions removal of solids, such as by filtration, would result in the desired liquid composition.

FIG. 3 depicts a phase diagram at −15° C. for the above defined composition F. As detailed in Example 2 this composition is prepared from 2-amino-2-methylbutyronitrile (Component A), 2-amino-2-methylpentanonitrile (Component B), and 2-amino-2-methyloctanonitrile (Component D). The phase diagram of FIG. 3 shows the percentages of each starting aminonitrile, which when reacted, results in a product composition which is 100% liquid, or about 50% liquid, or solid at −15° C. The circles represent 100% liquid, circles with a line through them represent about 50% liquid, and the solid black circles represent 100% solid.

FIG. 4 depicts a phase diagram at 7° C. for the above defined composition B as detailed in Example 3. This composition is prepared from 2-amino-2-methylbutyronitrile (Component A), 2-amino-2-methylheptanonitrile (Component E) and 2-amino-2-methyloctanonitrile (Component D). This phase diagram shows the percentages of each starting aminonitrile, which when reacted, results in a product composition which is 100% liquid (circles), about 50% liquid (circles with lines through them) and solid (black circles).

The liquid azodinitrile mixtures of this invention are useful in producing ethylene copolymers. High pressure copolymerizations of ethylene and vinyl acetate, methyl methacrylate, ethyl acrylate, acyclic and methacrylic acids and salts, vinyl chloride, acrylonitrile, olefins such as propylene, butene-1 and butadiene, dibutyl maleate, carbon monoxide and the like can be carried out easily and efficiently using the azodinitrile mixtures of this invention as polymerization initiators.

These new compositions are initiators for the polymerization or copolymerization of other unsaturated monomers such as alkenes, vinyl halides, vinyl esters, vinylidene halides, vinyl cyanides and alkenyl aromatic as well as curing agents for polyester resins, initiators for free radical initiated chemical reactions, blowing agents for producing foamed polymer and plastics and selective oxidizing agents.

Illustrative polymerizable monomers other than ethylene and ethylene-comonomers are vinyl chloride, vinylidene chloride, vinyl acetate, vinyl pyridine, vinyl pyrrolidone, vinyl carbazole, butadiene, isoprene, acrylonitrile, acyclic acid, acyclic acid esters, methacrylic acid, methacrylic acid esters, styrene, chlorostyrene and methyl styrenes.

The liquid azodinitrile mixtures of this invention are concentrated fluids and are useful full strength where desirable, convenient or necessary. Any organic solvent which is liquid under reaction conditions and inert with respect to the azodinitriles of this invention may be used as a diluent for the azodinitrile mixtures described herein. Some such suitable solvents include, for example, appropriate alcohols, aliphatic hydrocarbons, esters, glycol ethers, ketones, aliphatic petroleum naphthas, aromatic hydrocarbons, chlorinated aliphatic hydrocarbons, chlorinated aromatic hydrocarbons, amides, nitriles, or mixtures thereof.

The azodinitriles of the present invention are synthesized according to the procedure in U.S. Pat. No. 4,028,345, the teachings of which are hereby incorporated by reference. At least three aminonitriles are reacted with sodium hypochlorite solution and quaternary amine salts. The excess hypochlorite is neutralized with sodium bisulfite and the resulting liquid azo mixture is separated from the aqueous phase, washed with bicarbonate, and dried under vacuum.

In the process of the present invention, three molecules of an amino compound selected from the group consisting of

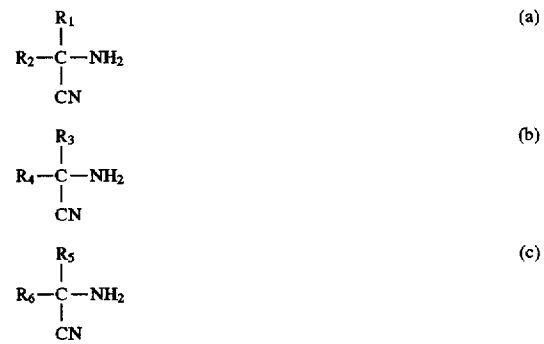

wherein $R_1$, $R_2$, $R_3$, $R_4$, $R_5$ and $R_6$ are each independently an acyclic aliphatic hydrocarbon radical of 1–9 carbon atoms, are reacted to form the azodinitrile of the present invention. The reaction is accomplished in an aqueous medium with a metal hypochlorite represented by the formula M(OCl)$_x$, wherein M is selected from sodium; potassium and calcium and x is the valence of the M ion, and a surface active compound selected from the group consisting of an anionic, cationic, nonionic, amphoteric and mixed surface active agents or surfactants. The equivalent ratio of hypochlorite to aminonitrile is not critical. However, at equivalent ratios below 1:1 of hypochlorite to aminonitrile the yield is less desirable. At equivalent ratios above 2:1 there is no advantage. Generally, the equivalent ratio of 1:1 to 2:1 will give high yields although the ratio of 1.2:1 to 1.8:1 is preferred because of the especially high yields that result. The equivalent ratio referred to herein is defined as the equivalent of metal hypochlorite per mole of aminonitrile. An equivalent of metal hypochlorite is a mole of the hypochlorite divided by the valence of the metal. An equivalent of aminonitrile is the same as the molar amount of aminonitrile.

The amino compounds used as starting materials may be selected from the formulas given above denoted (a) (b) and (c) or combinations thereof. The amino compounds can be prepared by methods well known in the art, for example, by the method described by Anderson in U.S. Pat. No. 2,711,405. A procedure that can be used to obtain the amino compounds involves charging an appropriate ketone to a platinum-lined pressure vessel and cooling this to dry ice-acetone temperature and then adding 5–10 grams of ammonia. Hydrogen cyanide is then introduced in portions in an amount equimolar to that of the ketone. The reaction vessel is warmed to room temperature and pressurized to 50 psig (34.5×10$^4$ Pa) with ammonia, heated to 40° C. and held at 40° C. and 50 psig (34.5×10$^4$ Pa) for 8 hours and finally cooled and the product is discharged from the vessel.

The hydrochlorite used in the present invention is a metal hydrochlorite represented by the formula M(OCl)$_x$ where M is selected from sodium, potassium and calcium and x is the valance of M. For reasons of convenience and economy, sodium hypochlorite is the preferred hypochlorite. Sodium hypochlorite can be prepared by passing chlorine gas in an aqueous sodium hydroxide solution at about 9° C. or it can be purchased commercially. Other hypochlorites can be prepared analogously.

The surface active compounds used in the present invention are defined as any compound or mixture of compounds that affects the surface tension when mixed with water and is not adversely affected in its properties if it reacts with the hypochlorite, aminonitrile, chloramine intermediate or final product of the present invention. The inclusion of a surfactant in the process of reacting aminonitriles to give an azodinitrile with hypochlorite enables the reaction to proceed in strictly aqueous medium.

Surfactants for preparing emulsions are discussed by Paul Becher in "Emulsions, Theory and Practice" ACS Monograph No. 162, 1965. On pages 232–255. Becher discusses the importance of the Hydrophilic-Lipophilic Balance of a surfactant (HLB) on its ability to serve as an emulsifying agent in a particular application. The HLB numbers which have been assigned to many surfactants indicate balance in their affinity for water (hydrophilic) or non-polar organic liquids (lipophilics). A high HLB number indicates high water solubility and low organic solubility, a low number indicates a high organic solubility and low water solubility.

The azodinitriles of the present invention can generally be produced with surfactants or mixtures thereof within the range of about 8.0 to about 35.0 HLB range. The surfactants or surface active agents useful in the present invention may be a mixture of said surfactants or surface active agents.

Thus, in surfactant mixtures, one component of the mixture may have a HLB number outside the range described herein as long as the HLB of the mixture is within said range.

The atomospheric pressure system is entirely aqueous, requiring no organic solvent to be present as a promoter or co-solvent with water. The surfactant is mixed with the water as is the sodium hypochlorite or other metal hypochlorite and the aminonitrile is added with sufficient cooling to handle the heat load.

During the reaction period, it is necessary to add an agent to destroy residual sodium hypochlorite, chloramines and other oxidizing impurities and thereby give a cleaner product. Sodium bisulfite serves this purpose, as well as gaseous or liquid $SO_2$. Acid such as hydrochloric or sulfuric is introduced during the product workup to enhance the activity of sodium bisulfite by converting it in part or whole to sulfur dioxide, a powerful reducing agent. Other inorganic salts may be employed.

Any concentration of sodium hypochlorite less than about 16% can be used, but 5–15% is preferred. With less than 5%, yields of product tend to drop off. However, calcium hypochlorite, which is available as a 100% active material, is diluted to attain the preferred 5–15% range. Potassium hypochlorite solutions of the above concentration can also be preferred.

The time required to complete the reaction is dependent on temperature. A typical temperature for the reaction is −10° C. to 30° C. At the preferred temperature range of 5°–15° C., the reaction takes from about 10 minutes to 30 minutes. At a temperature of −5° C., the reaction will take well over 1 hour. At 30° C., the reaction can be complete in 5 minutes. The time required for the reaction for a specific product at a specific temperature and batch size can readily be determined.

Azodinitriles compositions which exist in solid and liquid phases simultaneously at a particular temperature can be filtered to remove the solids. The resulting filtrate would be suitable for use as a polymerization initiator in the same manner as the compositions of the present invention.

The present invention is further illustrated by the examples below.

EXAMPLES

For all examples the percent solids were determined as follows. Samples were placed in glass ampoules and stored at the recorded temperatures for at least 72 hours. Solids were visually estimated relative to the entire amount of sample present in the ampoule (i.e. and layer of solid occupying one tenth of the ampoule was designated 10% solids).

Example 1

To a 1.0-liter beaker equipped with a motor-driven Teflon-coated stirrer, thermocouple, 100-ml addition funnel, and situated in a dry ice-acetone cooling bath, 286.7 g (0.5665 moles) of 14.71% sodium hypochlorite were added along with 1.54 g of dioctyldimethyl ammonium chloride. The temperature was lowered to 7° C. and a mixture of aminonitriles consisting of 20 g (0.20389 moles) 2-amino-2-methylbutanonitrile (MEK), 10 g (0.0891 moles) amino-2-methylpentanonitrile (MPK), and 20 g (0.1429 moles) 2-amino-2-methylheptanonitrile (MAK) which had been sparged of excess ammonia for one hour at 35° C., were added over a 50 minute period. After the addition, the temperature was held at 7° C. for 30 minutes followed by neutralization of excess hypochlorite with 20 g of sodium bisulfite while the pH was maintained above 9 with the addition of 3.1 g of 10N sodium hydroxide. The liquid organic layer was then separated from the more dense aqueous phase and subsequently washed with 5% sodium bicarbonate. After 2 additional washes and separations with deionized water, the crude product was dried under vacuum (10 mm Hg, $13.3 \times 10^2$ Pa) for 2 hours. Final purity by gas evolution and gas chromatography, 98%. Final yield 91%. Liquid at $-15°$ C.

The product mixture contained:

Butanenitrile, 2,2'-azobis(2-methyl-Pentanenitrile, 2,2'-azobis(2-methyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Pentanenitrile, 2-[(1-cyano-1-methylpropyl)azo]-2-methyl

| Reactants, % | | | | | | | | | | | | | | |
|---|---|---|---|---|---|---|---|---|---|---|---|---|---|---|
| MEK | 70 | 65 | 55 | 54 | 50 | 45 | 40 | 40 | 37 | 35 | 33 | 25 | 25 | 15 |
| MPK | 15 | 10 | 20 | 12 | 12.5 | 10 | 40 | 20 | 13 | 5 | 33 | 25 | 20 | 20 |
| MAK | 15 | 25 | 25 | 34 | 37.5 | 45 | 20 | 40 | 50 | 60 | 33 | 50 | 55 | 65 |
| % Yield | 82 | 76 | 82 | 90 | 89 | 91 | 87 | 91 | 93 | 91 | 90 | 87 | 88 | 93 |
| % Purity | 94 | 97 | 97 | 98 | 93 | 95 | 96 | 96 | 91 | 90 | 96 | 95 | 94 | 88 |
| Form | S | S | S | S | L | L | S | L | L | S | S | S | S | S |

This data is represented on FIG. 1. S indicates solid, L indicates liquid, and 50% L indicates 50% liquid.

The following examples were completed following the procedure given in Example 1, using the aminonitriles indicated on a percentage by weight basis. The form is indicated using the above defined abbreviations.

Example 2

| Reactant, % | | | | | | | |
|---|---|---|---|---|---|---|---|
| 2-Amino-2-methyl-butyronitrile | 33 | 40 | 20 | 40 | 50 | 25 | 25 |
| 2-Amino-2-methyl-pentanonitrile | 33 | 20 | 40 | 40 | 25 | 50 | 25 |
| 2-Amino-2-methyl-octanonitrile | 33 | 40 | 40 | 20 | 25 | 25 | 50 |
| % Yield | 94.5 | 87.5 | 86.9 | 87.8 | 73 | 86.8 | 87 |
| % Purity | 96.3 | 96.0 | 99.6 | 92.0 | 97.3 | 96.9 | 99.2 |
| Form | S | 50% L | L | S | 50% L | S | S |

This data is represented on FIG. 3.

Product Mixture:

Butanenitrile, 2,2'-azobis(2-methyl-Pentanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylbutyl)azo]-2-methyl-Pentanenitrile, 2-[(1-cyano-1-methylpropyl)azo]-2-methyl

Example 3

| Reactant, % | | | | | | | |
|---|---|---|---|---|---|---|---|
| 2-Amino-2-methyl-butyronitrile | 33 | 20 | 40 | 40 | 50 | 25 | 25 |
| 2-Amino-2-methyl-heptanonitrile | 33 | 40 | 20 | 40 | 25 | 50 | 25 |
| 2-Amino-2-methyl-octanonitrile | 33 | 40 | 40 | 20 | 25 | 25 | 50 |
| % Yield | 79 | 62.8 | 87.3 | 89.7 | 82.5 | 54.0 | 90.9 |
| % Purity | 94.8 | 98.13 | 89.4 | 99.9 | 99.9 | 98.1 | 98.3 |
| Form | L | L | L | 50% L | 50% L | S | S |

This data is represented in FIG. 4

Product Mixture:

Butanenitrile, 2,2'-azobis(2-methyl-Heptanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylhexyl)azo]-2-methyl-Heptanenitrile, 2-[(1-cyano-1-methylpropyl)azo]-2-methyl

Example 4

| Reactants: | |
|---|---|
| 2-Amino-2-methylbutyronitrile | 33% |
| 2-Amino-2-methylpentanonitrile | 33% |
| 2-Amino-2-ethylbutyronitrile | 33% |

Yield=88.3%

Purity=93.1%

33% solid at 25° C.

100% solid at 0° C.

Product Mixture:

Butanenitrile, 2,2'-azobis(2-methyl-Pentanenitrile, 2,2'-azobis(2-methyl-Butanenitrile, 2,2'-azobis(2-ethyl-Pentanenitrile, 2-[(1-cyano-1-methylpropyl)azo]-2-methyl-Pentanenitrile, 2-[(1-cyano-1-ethylpropyl)azo]-2-methyl-Butanenitrile, 2-[(1-cyano-1-methylpropyl)azo]-2-ethyl

Example 5

| Reactants: | |
|---|---|
| 2-Amino-2-methylbutyronitrile | 21% |
| 2-Amino-2,4-dimethylpentanonitrile | 26% |
| 2-Amino-2-methylpentanonitrile | 24% |
| 2-Amino-2-methylheptanonitrile | 29% |

Yield 95%,

Purity 93%,

Liquid at 0° C.

100% solids at $-15°$ C.

Product Mixture:

Butanenitrile, 2,2'-azobis(2-methyl-Pentanenitrile, 2,2'-azobis(2-methyl-Pentanenitrile, 2,2'-azobis(2,4-dimethyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Heptanenitrile, 2-[(1-cyano-1,3-dimethylbutyl)azo]-2-methyl-Pentanenitrile, 2-[(1-cyano-1-methylbutyl)azo]-2,4-dimethyl-Pentanenitrile, 2-[(1-cyano-1-methylpropyl)azo]-2-methyl-Pentanenitrile, 2-[(1-cyano-1-methylpropyl)azo]-2,4-dimethyl Example 6

| Reactants: | |
|---|---|
| 2-Amino-2-methylpentanonitrile | 33% |
| 2-Amino-2-methylheptanonitrile | 33% |
| 2-Amino-2-methyloctanonitrile | 33% |

Purity=93%
Liquid at 25° C.
100% Solid at 0° C.
Product Mixture:

Pentanenitrile, 2,2'-azobis(2-methyl-Heptanenitrile, 2,2'-azobis(2-methyl-Octanenitrile, 2,2'-azobis(2-methyl-Octanenitrile, 2-[(1-cyano-1-methylbutyl)azo]-2-methyl-Octanenitrile, 2-[(1-cyano-1-methylhexyl)azo]-2-methyl-Heptanenitrile, 2-[(1-cyano-1-methylbutyl)azo]-2-methyl Example 7

| Reactants: | |
|---|---|
| 2-Amino-2-methylbutanonitrile | 25% |
| 2-Amino-2-ethylbutanonitrile | 25% |
| 2-Amino-2-methylpentanonitrile | 25% |
| 2-Amino-2-methylheptanonitrile | 25% |

Yield=85%
Purity=97%
Liquid at 25° C.
Liquid at -15° C.
Product Mixture:

Butanenitrile, 2,2'-azobis(2-methyl-Pentanenitrile, 2,2'-azobis(2-methyl-Butanenitrile, 2,2'-azobis(2-ethyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Heptanenitrile, 2-[(1-cyano-1-ethylpropyl)azo]-2-methyl-Pentanenitrile, 2-[(1-cyano-1-methylpropyl)azo]-2-methyl-Pentanenitrile, 2-[(1-cyano-1-ethylpropyl)azo]-2-methyl-Butanenitrile, 2-[(1-cyano-1-methylpropyl)azo]-2-ethyl Comparative Example A

| Reactants: | |
|---|---|
| 2-Amino-2-methylbutyronitrile | 25% |
| 2-Amino-2-methylpropanonitrile | 25% |
| 2-Amino-2-methylpentanonitrile | 25% |
| 2-Amino-2-methylheptanonitrile | 25% |

Yield 56%.
Purity 96%, 10% solids at 25° C.
75% solids at 0° C.
100% solids at -15° C.
Product Mixture:

Propanenitrile, 2,2'-azobis(2-methyl-Butanenitrile, 2,2'-azobis(2-methyl-Pentanenitrile, 2,2'-azobis(2-methyl-Heptanenitrile, 2,2'-azobis(2-methyl-Heptanenitrile, 2-[(1-cyano-1-methylethyl)azo]-2-methyl-Heptanenitrile, 2-[(1-cyano-1-methylpropyl)azo]-2-methyl-Heptanenitrile, 2-[(1-cyano-1-methylbutyl)azo]-2-methyl-Pentanenitrile, 2-[(1-cyano-1-methylethyl)azo]-2-methyl-Pentanenitrile, 2-[(1-cyano-1-methylpropyl)azo]-2-methyl-Butanenitrile, 2-[(1-cyano-1-methylethyl)azo]-2-methyl Comparative Example B

| Reactants: | |
|---|---|
| 2-Amino-2-methylbutyronitrile | 33% |
| 1-Amino cyclohexano carbonitrile | 33% |
| 2-Amino-2-methylheptanonitrile | 33% |

Yield 80%.
Purity 96%, 20% solids at 25° C.
60% solids at -15° C.
Product Mixture:

Butanenitrile, 2,2'-azobis(2-methyl-Cyclohexanecarbonitrile, 1,1'-azobis-Heptanenitrile, 2,2'-azobis(2-methyl-Heptanenitrile, 2-[(cyanocyclohexane)azo]-2-methyl-Heptanenitrile, 2-[(1-cyano-1-methylpropyl)azo]-2-methyl-Cyclohexanecarbonitrile, 2-[(1-cyano-1-methylpropyl)azo]

Comparative Example C

| Reactants: | |
|---|---|
| 2-Amino-2-methylbutyronitrile | 33% |
| 1-Amino cyclohexano carbonitrile | 33% |
| 2-Amino-2-methylpentanonitrile | 33% |

Yield 70%.
Purity 94%, 30% solids at 25° C.
100% solids at -15° C.
Product Mixture:

Butanenitrile, 2,2'-azobis(2-methyl-Cyclohexanecarbonitrile, 1,1'-azobis-Pentanenitrile, 2,2'-azobis(2-methyl-Cyclohexanecarbonitrile, 2-[(1-cyano-1-methylpropyl)azo]-Cyclohexanecarbonitrile, 2-[(1-cyano-1-methylbutyl)azo]-Pentanenitrile, 2-[(1-cyano-1-methylpropyl)azo]-2-methyl

What is claimed is:

1. An azodinitrile composition comprising a mixture of at least six different azodinitriles of formula I

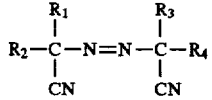

wherein
$R_1$, $R_2$, $R_3$, and $R_4$ are each independently selected from the group consisting of acyclic aliphatic hydrocarbon radicals of 1–9 carbon atoms, said mixture having a freezing point of a maximum of 25° C.

2. The composition of claim 1 having a freezing point of a maximum of 0° C.

3. The composition of claim 1 having a freezing point of a maximum of −15° C.

4. The composition of claim 1 wherein $R_1$, $R_2$, $R_3$, and $R_4$ are each independently selected from the group consisting of methylbutyro, methylpentano, methylheptano, methyloctano, ethylbutano, cyanomethylpropyl, cyanomethylbutyl, and cyanodimethylbutyl.

5. An azodinitrile composition selected from the group consisting of mixtures A and B:

A. Butanenitrile, 2,2'-azobis(2-methyl-Pentanenitrile, 2,2'-azobis(2-methyl-Butanenitrile, 2,2'-azobis(2-ethyl-Pentanenitrile, 2-[(1-cyano-1-methylpropyl)azo]-2-methyl-Pentanenitrile, 2-[(1-cyano-1-ethylpropyl)azo]-2-methyl-Butanenitrile, 2-[(1-cyano-1-methylpropyl)azo]-2-ethyl B. Butanenitrile, 2,2'-azobis(2-methyl-Heptanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylhexyl)azo]-2-methyl-Heptanenitrile, 2-[(1-cyano-1-methylpropyl)azo]-2-methyl said composition having a freezing point of a maximum of 25° C.

6. An azodinitrile composition selected from the group consisting of mixtures C and D C. Pentanenitrile, 2,2'-azobis(2-methyl-Butanenitrile, 2,2'-azobis(2-ethyl-Heptanenitrile, 2,2'-azobis(2-methyl-Heptanenitrile, 2-[(1-cyano-1-methylbutyl)azo]-2-methyl-Heptanenitrile, 2-[(1-cyano-1-ethylpropyl)azo]-2-methyl-Pentanenitrile, 2-[(1-cyano-1-ethylpropyl)azo]-2-methyl D. Butanenitrile, 2,2'-azobis(2-methyl-Pentanenitrile, 2,2'-azobis(2-methyl-Pentanenitrile, 2,2'-azobis(2,4-dimethyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Heptanenitrile, 2-[(1-cyano-1,3-dimethylbutyl)azo]-methyl-Pentanenitrile, 2-[(1-cyano-1-methylbutyl)azo]-2,4-dimethyl-Pentanenitrile, 2-[(1-cyano-1-methylpropyl)azo]-2-methyl-Pentanenitrile, 2-[(1-cyano-1-methylpropyl)azo]-2,4-dimethyl said composition having a freezing point of a maximum of 0° C.

7. An azodinitrile composition selected from the group consisting of mixtures E, F and G.

E. Butanenitrile, 2,2'-azobis(2-methyl-Pentanenitrile, 2,2'-azobis(2-methyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Pentanenitrile, 2-[(1-cyano-1-methylpropyl)azo]-2-methyl F. Butanenitrile, 2,2'-azobis(2-methyl-Pentanenitrile, 2,2'-azobis(2-methyl-Octanenitrile, 2,2'-azobis(2-methyl-Octanenitrile, 2-[(1-cyano-1-methylbutyl)azo]-2-methyl-Pentanenitrile, 2-[(1-cyano-1-methylpropyl)azo]-2-methyl G. Butanenitrile, 2,2'-azobis(2-methyl-Pentanenitrile, 2,2'-azobis(2-methyl-Butanenitrile, 2,2'-azobis(2-ethyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Heptanenitrile, 2-[(1-cyano-1-ethylpropyl)azo]-2-methyl-Pentanenitrile, 2-[(1-cyano-1-methylpropyl)azo]-2-methyl-Pentanenitrile, 2-[(1-cyano-1-ethylpropyl)azo]-2-methyl-Butanenitrile, 2-[(1-cyano-1-methylpropyl)azo]-2-ethyl said composition having a freezing point of a maximum of −15° C.

8. A process for the preparation of azodinitrile mixtures comprising reacting three or more different aminonitriles of formula

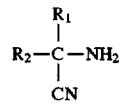

wherein $R_1$ and $R_2$ are each independently selected from the group consisting of acyclic aliphatic hydrocarbon radicals of 1–9 carbon atoms, with 5% to 15% by weight based on the reaction mixture of a metal hypochlorite, $M(OCl)x$, wherein M is selected from the group consisting of sodium, potassium, or calcium, and x is the valence of M, in an aqueous medium in the presence of 0.25 to 10% by weight based on the weight of aminonitrile of a surface active compound or mixtures thereof having a hydrophilic-lipophilic balance of 8 to 35 at a temperature of −10° C. to 30° C., said metal hypochlorite and alpha-aminonitrile being present in an equivalent ratio of from 1:1 to 2:1 of hypochlorite to aminonitrile and recovering from the reaction product a mixture of aliphatic azodinitrile compounds of the formula

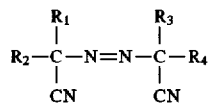     I wherein $R_1$, $R_2$, $R_3$, and $R_4$ independently selected from the group consisting of acyclic aliphatic hydrocarbon radicals of 1–9 carbon atoms.

* * * * *

UNITED STATES PATENT AND TRADEMARK OFFICE
CERTIFICATE OF CORRECTION

PATENT NO. : 5,760,192
DATED : June 2, 1998
INVENTOR(S) : Ernest Byron Wysong

It is certified that error appears in the above-identified patent and that said Letters Patent is hereby corrected as shown below:

Column 2, lines 62-67, delete "Butanenitrile, 2,2'-azobis(2-methyl-Pentanenitrile, 2,2'-azobis(2-methyl-Heptanenitrile, 2,2'-azobis(2-methyl-Heptanenitrile, 2-[(1-cyano-1-methylpropyl)azo]-2-methylHeptanenitrile, 2-[(1-cyano-1-methylbutyl)azo]-2-methyl-Pentanenitrile, 2-[(1-cyano-1-methylpropyl)azo]-2-methyl" and insert -- Butanenitrile, 2,2'-azobis(2-methyl-; Pentanenitrile, 2,2'-azobis(2-methyl-; Heptanenitrile, 2,2'-azobis(2-methyl-; Heptanenitrile, 2-[(1-cyano-1-methylpropyl)azo]-2-methyl-; Heptanenitrile, 2-[(1-cyano-1-methylbutyl)azo]-2-methyl; Pentanenitrile, 2-[(1-cyano-1-methylpropyl)azo]-2-methyl-. --

Column 3, lines 8-13, delete "Butanenitrile, 2,2'-azobis(2-methyl-Pentanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylbutyl)azo]-2-methyl-Pentanenitrile, 2-[(1-cyano-1-methylpropyl)azo]-2-methyl" and insert -- Butanenitrile, 2,2'-azobis(2-methyl-; Pentanenitrile, 2,2'-azobis(2-methyl-; Octanenitrile, 2,2'-azobis(2-methyl-; Octanenitrile, 2-[(1-cyano-1-methylpropyl)azo]-2-methyl-; Octanenitrile, 2-[(1-cyano-1-methylbutyl)azo]-2-methyl-; Pentanenitrile, 2-[(1-cyano-1-methylpropyl)azo]-2-methyl-. --

UNITED STATES PATENT AND TRADEMARK OFFICE
CERTIFICATE OF CORRECTION

PATENT NO. : 5,760,192
DATED : June 2, 1998
INVENTOR(S) : Ernest Byron Wysong

It is certified that error appears in the above-identified patent and that said Letters Patent is hereby corrected as shown below:

Column 3, lines 18-23, delete "Butanenitrile, 2,2'-azobis(2-methyl-Heptanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylhexyl)azo]-2-methyl-Heptanenitrile, 2-[(1-cyano-1-methylpropyl)azo]-2-methyl" and insert -- Butanenitrile, 2,2'-azobis(2-methyl-; Heptanenitrile, 2,2'-azobis(2-methyl-; Octanenitrile, 2,2'-azobis(2-methyl-; Octanenitrile, 2-[(1-cyano-1-methylpropyl)azo]-2-methyl-; Octanenitrile, 2-[(1-cyano-1-methylhexyl)azo]-2-methyl-; Heptanenitrile, 2-[(1-cyano-1-methylpropyl)azo]-2-methyl-. --

Column 4, lines 28-32, delete "Suitable acyclic aliphatic hydrocarbon radicals for $R_1$, $R_2$, $R_3$, $R_4$, $R_5$ and $R_6$ include, for example, methylbutyro, methylpentano, methylheptano, methyloctano, ethylbutano, cyanomethylpropyl, cyanomethylbutyl, and cyanodimethylbutyl." and insert -- Suitable acyclic aliphatic hydrocarbon radicals for $R_1$-C-$R_2$, $R_3$-C-$R_4$, and $R_5$-C-$R_6$ include, for example, methylbutyro, methylpentano, methylheptano, methyloctano, ethylbutano, cyanomethylpropyl, cyanomethylbutyl, and cyanodimethylbutyl. --

Column 4, lines 36-41, delete "A. Butanenitrile, 2,2'-azobis(2-methyl-Pentanenitrile, 2,2'-azobis(2-methyl-Butanenitrile, 2,2'-azobis(2-ethyl-Pentanenitrile, 2-[(1-cyano-1-methylpropyl)azo]-2-methyl-Pentanenitrile, 2-[(1-cyano-1-ethylpropyl)azo]-2-methyl-Butanenitrile, 2-[(1-cyano-1-methylpropyl)azo]-2-ethyl" and insert - A. Butanenitrile, 2,2'-azobis(2-methyl-; Pentanenitrile, 2,2'-azobis(2-methyl-; Butanenitrile, 2,2'-azobis(2-ethyl-; Pentanenitrile, 2-[(1-cyano-1-methylpropyl)azo]-2-methyl-; Pentanenitrile, 2-[(1-cyano-1-ethylpropyl)azo]-2-methyl-; Butanenitrile, 2-[(1-cyano-1-methylpropyl)azo]-2-ethyl-. --

UNITED STATES PATENT AND TRADEMARK OFFICE
CERTIFICATE OF CORRECTION

PATENT NO. : 5,760,192
DATED : June 2, 1998
INVENTOR(S) : Ernest Byron Wysong

It is certified that error appears in the above-identified patent and that said Letters Patent is hereby corrected as shown below:

Column 4, lines 44-49, delete "B. Butanenitrile, 2,2'-azobis(2-methyl-Heptanenitrile, 2,2'-azobis(2-methyl-Octanenitrile, 2,2'-azobis(2-methyl-Octanenitrile, 2-[(1-cyano-1-methylpropyl)azo]-2-methyl-Octanenitrile, 2-[(1-cyano-1-methylhexyl)azo]-2-methyl-Heptanenitrile, 2-[(1-cyano-1-methylpropyl)azo]-2-methyl" and insert
-- B. Butanenitrile, 2,2'-azobis(2-methyl-; Heptanenitrile, 2,2'-azobis(2-methyl-; Octanenitrile, 2,2'-azobis(2-methyl-; Octanenitrile, 2-[(1-cyano-1-methylpropyl)azo]-2-methyl-; Octanenitrile, 2-[(1-cyano-1-methylhexyl)azo]-2-methyl-; Heptanenitrile, 2-[(1-cyano-1-methylpropyl)azo]-2-methyl-. --

Column 4, lines 53-58, delete "C. Pentanenitrile, 2,2'-azobis(2-methyl-Butanenitrile, 2,2'-azobis(2-ethyl-Heptanenitrile, 2,2'-azobis(2-methyl-Heptanenitrile, 2-[(1-cyano-1-methylbutyl)azo]-2-methyl-Heptanenitrile, 2-[(1-cyano-1-ethylpropyl)azo]-2-methyl-Pentanenitrile, 2-[(1-cyano-1-ethylpropyl)azo]-2-methyl" and insert
-- C. Pentanenitrile, 2,2'-azobis(2-methyl-; Butanenitrile, 2,2'-azobis(2-ethyl-; Heptanenitrile, 2,2'-azobis(2-methyl-; Heptanenitrile, 2-[(1-cyano-1-methylbutyl)azo]-2-methyl-; Heptanenitrile, 2-[(1-cyano-1-ethylpropyl)azo]-2-methyl-; Pentanenitrile, 2-[(1-cyano-1-ethylpropyl)azo]-2-methyl-; --

UNITED STATES PATENT AND TRADEMARK OFFICE
CERTIFICATE OF CORRECTION

PATENT NO. : 5,760,192
DATED : June 2, 1998
INVENTOR(S) : Ernest Byron Wysong

It is certified that error appears in the above-identified patent and that said Letters Patent is hereby corrected as shown below:

Column 4, lines 59-67, delete "D. Butanenitrile, 2,2'-azobis(2-methyl-Pentanenitrile, 2,2'-azobis(2-methyl-Pentanenitrile, 2,2'-azobis(2,4-dimethyl-Heptanenitrile, 2,2'-azobis(2-methyl-Heptanenitrile, 2-[(1-cyano-1-methylpropyl)azo]-2-methyl-Heptanenitrile, 2-[(1-cyano-1-methylbutyl)azo]-2-methyl-Heptanenitrile, 2-[(1-cyano-1,3-dimethylbutyl)azo]-2-methyl-Pentanenitrile, 2-[(1-cyano-1-methylbutyl)azo]-2,4-dimethyl-Pentanenitrile, 2-[(1-cyano-1-methylpropyl)azo]-2-" and insert
-- D. Butanenitrile, 2,2'-azobis(2-methyl-; Pentanenitrile, 2,2'-azobis(2-methyl-; Pentanenitrile, 2,2'-azobis(2,4-dimethyl-; Heptanenitrile, 2,2'-azobis(2-methyl-; Heptanenitrile, 2-[(1-cyano-1-methylpropyl)azo]-2-methyl-; Heptanenitrile, 2-[(1-cyano-1-methylbutyl)azo]-2-methyl-; Heptanenitrile, 2-[(1-cyano-1,3-dimethylbutyl)azo]-2-methyl-; Pentanenitrile, 2-[(1-cyano-1-methylbutyl)azo]-2,4-dimethyl;- Pentanenitrile, 2-[(1-cyano-1-methylpropyl)azo]-2-. --

Column 5, lines 1-2, delete "methyl-Pentanenitrile, 2-[(1-cyano-1-methylpropyl)azo]-2,4-dimethyl" and insert -- methyl-; Pentanenitrile, 2-[(1-cyano-1-methylpropyl)azo]-2,4-dimethyl-. --

Signed and Sealed this

Eleventh Day of May, 1999

Attest:

Q. TODD DICKINSON

Attesting Officer

Acting Commissioner of Patents and Trademarks